(12) United States Patent
Cho et al.

(10) Patent No.: US 9,074,995 B2
(45) Date of Patent: Jul. 7, 2015

(54) MAGNETOSTRICTIVE PHASED ARRAY TRANSDUCER FOR TRANSDUCING SHEAR HORIZONTAL BULKWAVES

(71) Applicant: Korea Research Institute of Standards and Science, Daejeon (KR)

(72) Inventors: Seung Hyun Cho, Daejeon (KR); Bong Young Ahn, Daejeon (KR); Tae Hoon Heo, Busan (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 393 days.

(21) Appl. No.: 13/672,198

(22) Filed: Nov. 8, 2012

(65) Prior Publication Data

US 2013/0145851 A1    Jun. 13, 2013

(30) Foreign Application Priority Data

Dec. 12, 2011    (KR) .......................... 10-2011-0132533

(51) Int. Cl.

| | |
|---|---|
| *G01N 29/04* | (2006.01) |
| *H04R 15/00* | (2006.01) |
| *G01N 29/22* | (2006.01) |
| *G01N 29/26* | (2006.01) |
| *G01N 29/24* | (2006.01) |
| *B06B 1/08* | (2006.01) |

(52) U.S. Cl.
CPC .......... *G01N 29/262* (2013.01); *G01N 29/2412* (2013.01); *G01N 2291/0425* (2013.01); *G01N 2291/106* (2013.01); *B06B 1/085* (2013.01)

(58) Field of Classification Search
CPC ...... B06B 1/00; G01N 29/04; G01N 29/2412; G01N 29/262

USPC ............................................................. 73/643
See application file for complete search history.

(56) References Cited

U.S. PATENT DOCUMENTS

| | | | | |
|---|---|---|---|---|
| 4,273,968 | A * | 6/1981 | Suyama ........................ | 381/421 |
| 6,697,298 | B1 * | 2/2004 | Dubinsky et al. ............... | 367/81 |
| 7,913,562 | B2 * | 3/2011 | Kwun et al. .................... | 73/622 |
| 8,305,074 | B2 * | 11/2012 | Lee et al. ...................... | 324/209 |
| 8,354,842 | B2 * | 1/2013 | Kim et al. ..................... | 324/240 |

FOREIGN PATENT DOCUMENTS

KR    10-1061226    7/2011

* cited by examiner

*Primary Examiner* — J M Saint Surin
(74) *Attorney, Agent, or Firm* — Lowe Hauptman & Ham, LLP

(57) ABSTRACT

A magnetostrictive phased array transducer for transducing shear horizontal bulkwaves including a plurality of magnetostrictive members each having a bottom surface of a plate-shaped structure made of a ferromagnetic material, which is mounted to be adhered closely to the surface of a mounting place; an insulator disposed on a side surface of each magnetostrictive member; a meander coil having a plurality of coil lines extended in the direction parallel with the bottom surface on each insulator, wherein adjacent coil lines are connected so that current flows in the opposite directions to each other, thereby generating a dynamic magnetic field with respect to each magneto strictive member; and a magnet mounted to generate a static magnetic field perpendicular to the dynamic magnetic field. When the current is supplied to the meander coil, a plurality of magnetostrictive members generate a plurality of shear horizontal bulkwaves while being deformed by the magnetostriction effect.

16 Claims, 7 Drawing Sheets

MAGNETOSTRICTIVE PHASED ARRAY TRANSDUCER FOR TRANSDUCING SHEAR HORIZONTAL BULKWAVES

CROSS-REFERENCE TO RELATED APPLICATION

This application claims under 35 U.S.C. §119(a) the benefit of Korean Patent Application No. 10-2011-0132533 filed Dec. 12, 2011, the entire contents of which are incorporated herein by reference.

BACKGROUND (a) Technical Field

The present invention relates to a phased array transducer using a magnetostrictive phenomenon. More particularly, the present invention relates to a phased array transducer which can transduce shear horizontal bulkwaves for forming multiple channels without using a separate waveguide or waveguide structure.

(b) Background Art

A magnetostrictive transducer module for transducing guided ultrasonic waves has been disclosed in Korean Patent No. 10-1061226 filed and registered by the applicant of the present invention. As disclosed in Korean Patent No. 10-1061226, various types and modes of guided ultrasonic waves may exist according to the shape of a separate waveguide or waveguide structure.

Particularly, in the waveguide or waveguide structure is implemented as a plate-shaped structure, two kinds of guided ultrasonic waves, i.e., Lamb waves and shear horizontal (SH) waves may be used according to the direction of medium displacement, and an infinite mode exists in each of the Lamb and SH waves.

Since the dispersion curves of modes in the SH wave do not intersect with one another, the separation of modes from a measured signal is relatively easy, and the speeds of the modes are sequential. Thus, the operation of identifying the modes can be easily performed. In the shear horizontal wave, only the SH0 mode exists at no more than cutoff frequency of the SH1 mode, and thus influence of other modes can be excluded. More importantly, the SH0 mode is the unique mode of nondispersive waves, of which speed is not changed depending on its frequency. For these reasons, the mode of the SH wave, particularly the SH0 mode is preferably used in a nondestructive test based on guide ultrasonic waves.

Like the magnetostrictive transducer module disclosed in Korean Patent No. 10-1061226, a magnetostrictive transducer module including coil is manufactured, so that it is possible to transduce an ultrasonic wave having a directional property in the guided ultrasonic waves.

However, it was conventionally difficult to generate an ultrasonic wave having a directional property desired by a user. In addition, a transducer or transducer module including a separate waveguide or waveguide structure was used as an array sensor to be connected to a certain place. Therefore, the reduction in efficiency due to the use of the waveguide was unavoidable.

Since the thickness of a magnetostrictive patch used in the conventional magnetostrictive transducer or magnetostrictive transducer module was thin, it was impossible to erect the magnetostrictive patch. Further, the magnetostrictive patch required a relatively wide area, and therefore, it was disadvantageous to use the magnetostrictive patch.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art. Accordingly, the present invention provides a magnetostrictive phased array transducer in which a plurality of magnetostrictive members mounted to be adhered closely to the surface of a mounting place are disposed to perform the function of a waveguide or waveguide structure, so that it is possible to transduce a plurality of shear horizontal bulkwaves that form multiple channels with respect to the mounting place through the magnetostriction effect.

In one aspect, the present invention provides a magnetostrictive phased array transducer for transducing shear horizontal bulkwaves, including: a plurality of magnetostrictive members each having a bottom surface of a plate-shaped structure made of a ferromagnetic material, which is mounted to be adhered closely to the surface of a mounting place; an insulator disposed on a side surface of each magnetostrictive member; a meander coil having a plurality of coil lines extended in the direction parallel with the bottom surface on each insulator, wherein adjacent coil lines are connected so that current flows in the opposite directions to each other, thereby generating a dynamic magnetic field with respect to each magnetostrictive member; and a magnet mounted to generate a static magnetic field perpendicular to the dynamic magnetic field, wherein, when the current is supplied to the meander coil, a plurality of magnetostrictive members generate a plurality of shear horizontal bulkwaves while being deformed by the magnetostriction effect.

In another aspect, the present invention provides a magnetostrictive phased array transducer for transducing shear horizontal bulkwaves, including: a plurality of magnetostrictive members each having a bottom surface of a plate-shaped structure made of a ferromagnetic material, which is mounted to be adhered closely to the surface of a mounting place; a flexible printed circuit board having a plurality of coil lines extended in the direction parallel with the bottom surface on a side surface of each magnetostrictive member, wherein adjacent coil lines are connected so that current flows in the opposite directions to each other, thereby generating a dynamic magnetic field with respect to each magnetostrictive member; and a magnet mounted to generate a static magnetic field perpendicular to the dynamic magnetic field, wherein, when the current is supplied to an electric wire connected to the flexible printed circuit board, a plurality of magnetostrictive members generate a plurality of shear horizontal bulkwaves while being deformed by the magnetostriction effect.

In a exemplary embodiment, the time taken for each shear horizontal bulkwave to be focused with respect to a measurement sample may be changed by adjusting the distance between the magnetostrictive members.

In another exemplary embodiment, the focusing direction of the shear horizontal bulkwaves with respect to the measurement sample may be changed by controlling a difference in time at which each magnetostrictive member generates a shear horizontal bulkwave.

In still another exemplary embodiment, the magnetostrictive phased array transducer may include a couplant filled in an empty space between the bottom surface and the surface of the mounting place.

In yet another exemplary embodiment, the magnetostrictive phased array transducer may include a rear member for performing a damping process on the magnetostrictive member.

In still yet another exemplary embodiment, the area of the surface opposite to the bottom surface may be formed narrower than that of the bottom surface so as to induce and offset diffused reflection of ultrasonic waves.

In a further exemplary embodiment, the surface opposite to the bottom surface may be formed in a saw-tooth shape so as to induce and offset diffused reflection of ultrasonic waves.

In another further exemplary embodiment, the magnetostrictive phased array transducer may include a yoke attached to the magnet so as to form a loop of the static magnetic field.

Other aspects and exemplary embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
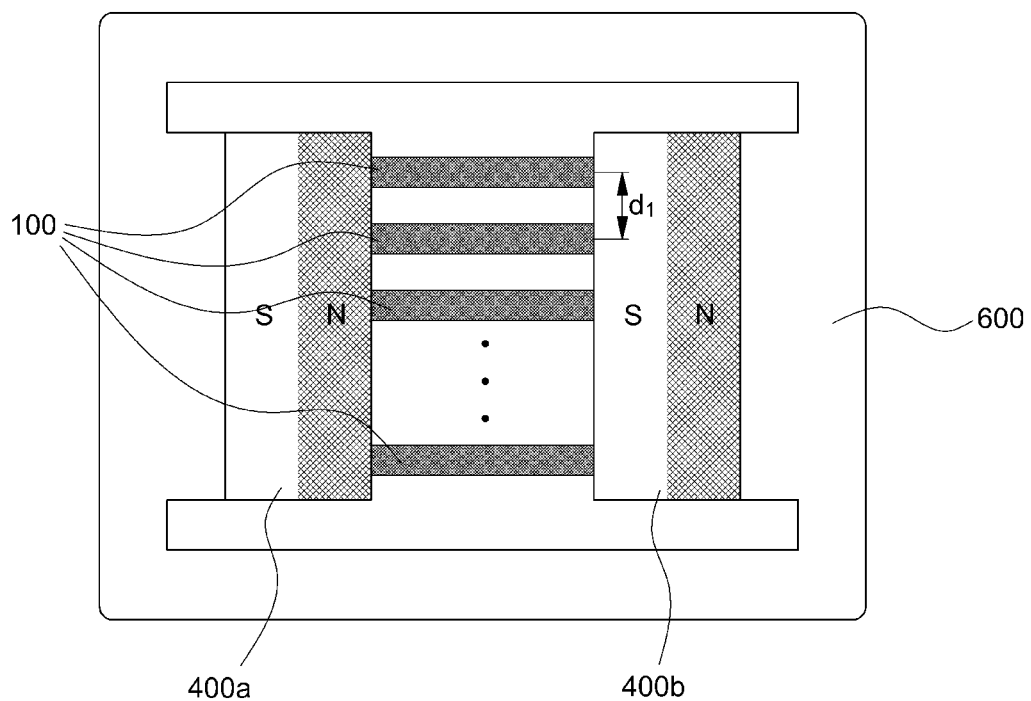
FIG. 1 is a plan view of a magnetostrictive phased array transducer for transducing shear horizontal bulkwaves according to the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Figure 2:
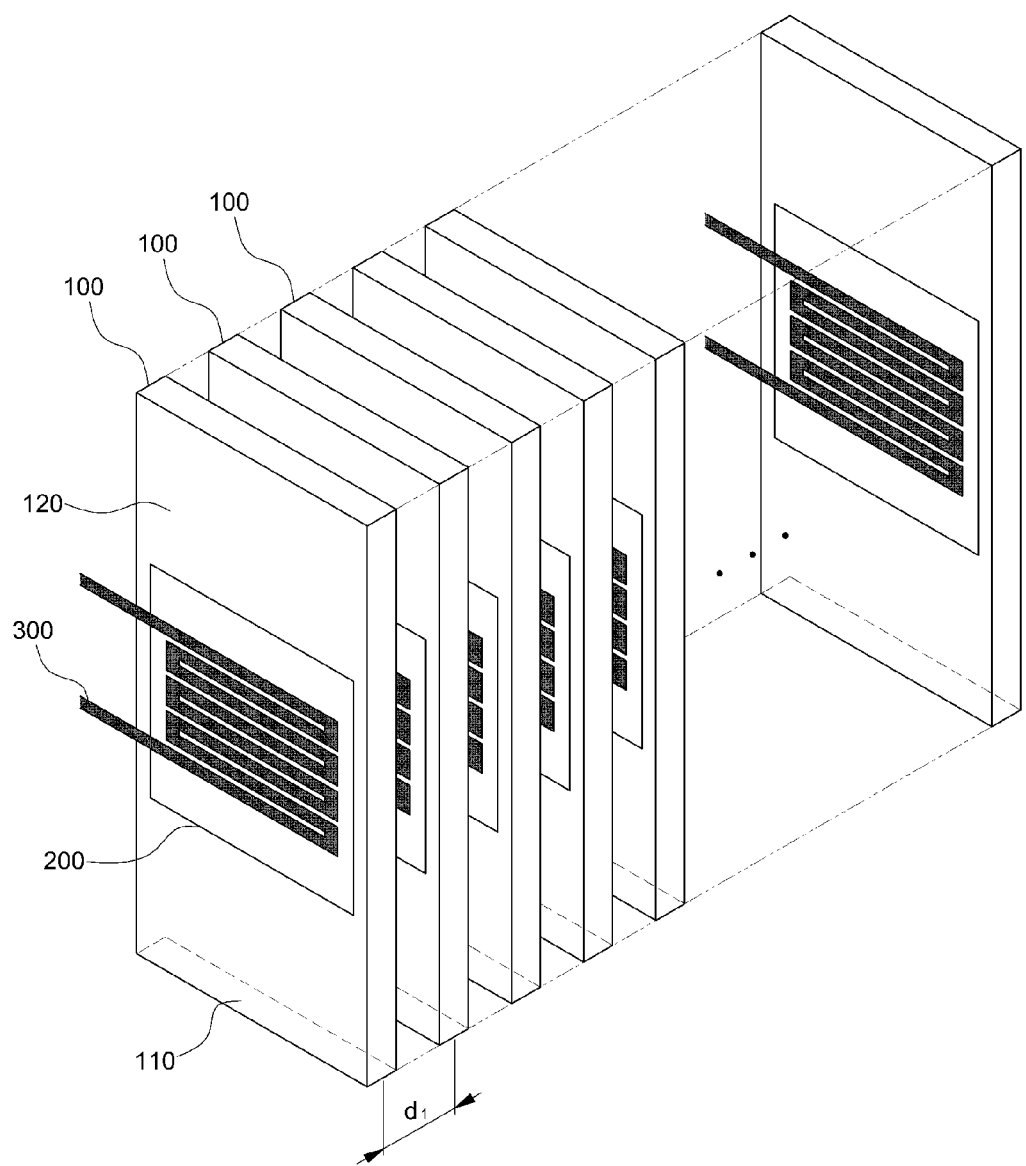
FIG. 2 is a perspective view of a plurality of magnetostrictive members in the magnetostrictive phased array transducer shown in FIG. 1 according to an embodiment of the present invention.

FIG. 1 is a plan view of a magnetostrictive phased array transducer for transducing shear horizontal bulkwaves according to the present invention. FIG. 2 is a perspective view of a plurality of magnetostrictive members in the magnetostrictive phased array transducer shown in FIG. 1 according to an embodiment of the present invention.

The magnetostrictive phased array transducer (MsPAT) for transducing shear horizontal bulkwaves according to the present invention includes a plurality of magnetostrictive members 100 each having a bottom surface 110 of a plate-shaped structure made of a ferromagnetic material, which is mounted to be adhered closely to the surface of a mounting place; an insulator 200 disposed on a side surface 120 of each magnetostrictive member 100; a meander coil 300 having a plurality of coil lines extended in the direction parallel with the bottom surface 110 on each insulator 200, wherein adjacent coil lines are connected so that current can flow in the opposite directions to each other, thereby generating a dynamic magnetic field with respect to each magnetostrictive member 100; and magnets 400a and 400b mounted to generate a static magnetic field perpendicular to the dynamic magnetic field. If the current is supplied to the meander coil 300, the magnetostrictive members 100 generate a plurality of shear horizontal bulkwaves while being deformed by the magnetostriction effect.

The magnetostrictive member 100 is formed in a plate-shaped structure, and the bottom surface 110 is mounted to be adhered closely to the surface of the mounting place. If a discontinuous plane caused by an air layer or roughness of the bottom surface 110 exists between the bottom surface 110 and the surface of the mounting place, the discontinuous plane causes an increase in impedance and reflects an ultrasonic wave generated. That is, a user does not measure the ultrasonic wave generated at the original position to be measured. Therefore, when the bottom surface 110 of the magnetostrictive member 100 is mounted on a surface of a sample, the bottom surface 110 of the magnetostrictive member 100 is preferably adhered closely to the surface of the sample so that the discontinuous plane does not exist. In this case, a couplant is preferably formed between the bottom surface 110 of the magnetostrictive member 100 and the surface of the sample so as to be filled in an empty space. A couplant known in the art may be used herein.

In the present invention, the bottom surface 110 of the magnetostrictive member 100 may come in line contact with the surface of the mounting place or may be formed in a convex shape having a certain volume so as to come in contact with the surface of the mounting place under a certain area. When being mounted on the mounting place, the MsPAT according to the present invention requires only a very small area or occupies only a minimum space. Thus, the size of a sensor entirely manufactured can be decreased, and the MsPAT can be mounted regardless of the shape or size of the mounting place.

Moreover, the MsPAT according to the present invention is configured to include a plurality of magnetostrictive members 100 and thus can generate a plurality of shear horizontal bulkwaves that form multiple channels. The time taken for each shear horizontal bulkwave to be focused on a specific portion or measurement sample may be changed by adjusting a distance $d_1$ between the magnetostrictive members 100. Here, the distance $d_1$ between the magnetostrictive members 100 is preferably set to λ/2 or less. The magnetostrictive member 100 is necessarily disposed at least every distance of λ/2 so that an image processed in a specific region can be obtained using a plurality of transduced shear horizontal bulkwaves.

In this case, a rear member is preferably formed on the bottom surface 110 of the magnetostrictive member 100 and the surface opposite to the bottom surface 110. The rear member is a member for performing a damping process, and can prevent the generated ultrasonic wave from being unnecessarily measured by being reflected with respect to the surface opposite to the bottom surface 110. In order to induce and offset diffused reflection of the ultrasonic wave, the magnetostrictive member 100 may be formed so that the area of the surface opposite to the bottom surface 110 is narrower than that of the bottom surface 110 or may be formed so that the surface opposite to the bottom surface has a saw-tooth shape.

As described above, in the present invention, a plurality of magnetostrictive members 100 are adhered closely to the surface of the mounting place so as to perform the function of a diaphragm or waveguide, so that a separate waveguide or waveguide structure is not required, thereby improving the efficiency of the MsPAT.

Further, the magnetostrictive member 100 is made of a ferromagnetic material. The magnetostrictive member is preferably made of a ferromagnetic substance such as iron (Fe), nickel (Ni) or cobalt (Co), an alloy thereof, or a material having a large magnetostriction amount.

The insulator 200 is a member that performs electrical insulation between the magnetostrictive member 100 and the meander coil 300 which will be described later. The insulator 200 is disposed on the side surface 120 of each magnetostrictive member 100. If the electrical insulation between the magnetostrictive member 100 and the meander coil 300 is possible, the shape or size of the insulator 200 is not limited.

Figure 3A:
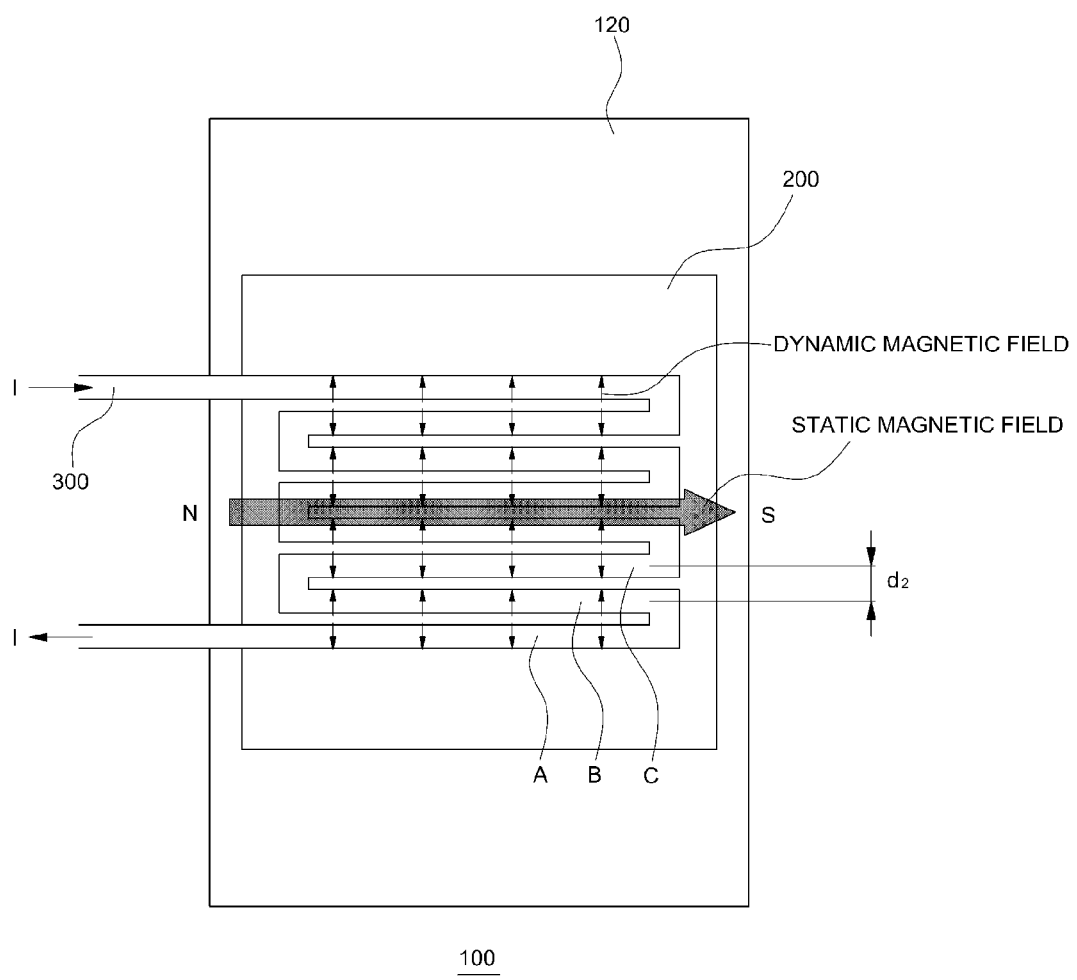
FIG. 3A is a side view of one of the plurality of magnetostrictive members shown in FIG. 2.

In the present invention, the meander coil 300 will be described in detail with reference to FIG. 3A. FIG. 3A is a side view of one of the plurality of magnetostrictive members shown in FIG. 2.

The meander coil 300 has a plurality of coil lines extended in the direction parallel with the bottom surface 110 on each insulator 200, and adjacent coil lines are connected so that current flows in the opposite directions to each other. As shown in FIG. 3A, the meander coil 300 includes a plurality of coil lines A, B, C and etc., and adjacent coil lines are connected to each other so as to form a zigzag shape. In other words, each coil line is extended in parallel with the bottom surface 110 of the magnetostrictive member 100, and end portions of the adjacent coil lines are connected to each other. In FIG. 3A, the meander coil 300 will be described based on the coil line B. One end portion of the coil line B is connected to one adjacent coil line A, and the other end portion of the coil line B is connected to another adjacent coil line C. Therefore, when current flows in the meander coil 300, the current flows in the opposite directions to each other in the adjacent coil lines.

The meander coil 300 generates a dynamic magnetic field with respect to the magnetostrictive member 100. If current I flows in the meander coil 300 as shown in FIG. 3A, dynamic magnetic fields are respectively generated in upper and lower directions (↑ and ↓) of the magnetostrictive member 100 according to the direction of the current. The dynamic magnetic fields are generated in a plurality of magnetostrictive members 100, respectively. In the meander coil 300, the distance $d_2$ between the adjacent coil lines is preferably adjusted to be equal to a half of the wavelength of the transduced shear horizontal bulkwave. This is because the shear horizontal bulkwaves are disposed not to be offset to each other and to cause reinforcement interference, so that it enables to reinforce a frequency component to be transduced and to offset other frequency components.

The magnets 400a and 400b are formed to generate a static magnetic field perpendicular to the dynamic magnetic field generated by the meander coil 300. As shown in FIG. 1, the magnets 400a and 400b may be respectively disposed at both sides with a plurality of magnetostrictive members 100 interposed therebetween so as to form a pair. As shown in FIG. 3A, a dynamic magnetic field is generated from the left surface to the right surface of each magnetostrictive member 100 so as to be in a relationship perpendicular to the dynamic magnetic field generated by the meander coil 300. Here, the magnets 400a and 400b may be disposed in any manner as long as the magnets 400a and 400b generate static magnetic fields in a relationship perpendicular to the dynamic magnetic fields generated with respect to a plurality of magnetostrictive members 100. The kind of the magnets 400a and 400b may be a permanent magnet or electromagnet. The static magnetic waves are preferably applied to the whole of the plurality of magnetostrictive members 100.

Figure 5:
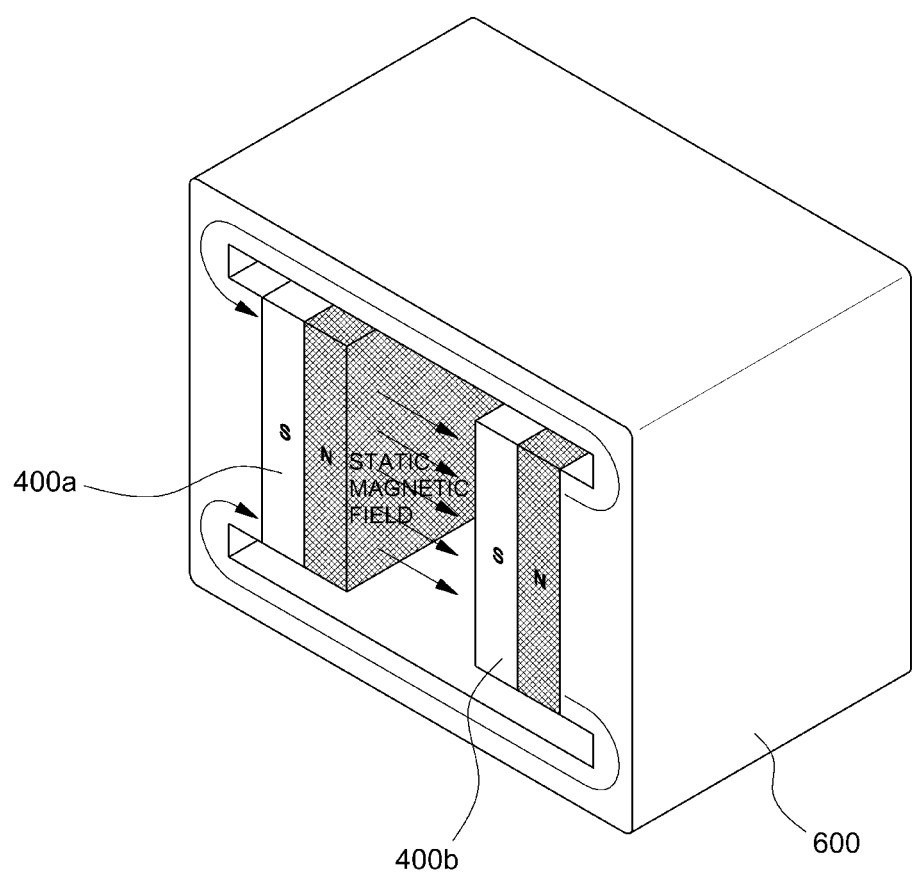
FIG. 5 is a perspective view of magnets and a yoke in the magnetostrictive phased array transducer shown in FIG. 1.

In addition, a yoke 600 is preferably attached to the magnets 400a and 400b. The yoke 600 is a member that is generally formed in the shape of a '⊏' or 'U' shape and serves as a passage through which magnetic forces smoothly move. The yoke 600 will be described with reference to FIG. 5. FIG. 5 is a perspective view of the magnets and the yoke in the MsPAT shown in FIG. 1.

The yoke 600 assists to form a loop of the static magnetic field generated by the magnets 400a and 400b, so that the static magnetic fields are effectively applied to a plurality of magnetostrictive members 100. The yoke 600 is preferably made of a material having high permeability, such as carbon steel, pure steel or silicon steel.

Figure 4:
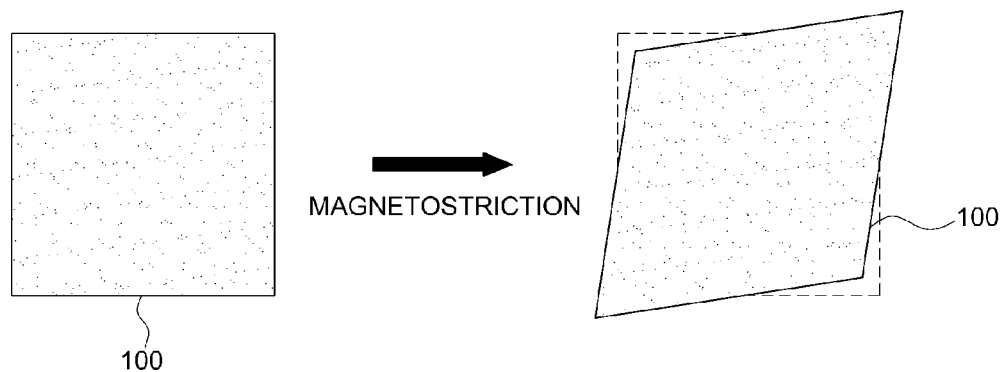
FIG. 4 is a schematic view illustrating a state in which a magnetostrictive member is transduced by the magnetostriction effect.

As described above, in the present invention, the dynamic magnetic field generated when the current is supplied to the meander coil 300 and the static magnetic field generated by the magnets 400a and 400b are perpendicular to each other. The relationship between the magnetic fields acts so that the magnetostrictive member 100 causes shear deformation as shown in FIG. 4. A plurality of shear horizontal bulkwaves generated at the mounting place by the shear deformation of the magnetostrictive member 100 may be used to detect the state of a position desired by the user or may be applied to various usages including a pulse-echo method, internal analysis through image processing for a measured sample, etc.

That is, a plurality of shear horizontal bulkwaves are generated not only on the surface of the mounting place but also in all directions including an internal direction, and the analysis for the measured sample positioned at various places can be performed by focusing a plurality of generated shear horizontal bulkwaves.

Figure 3B:
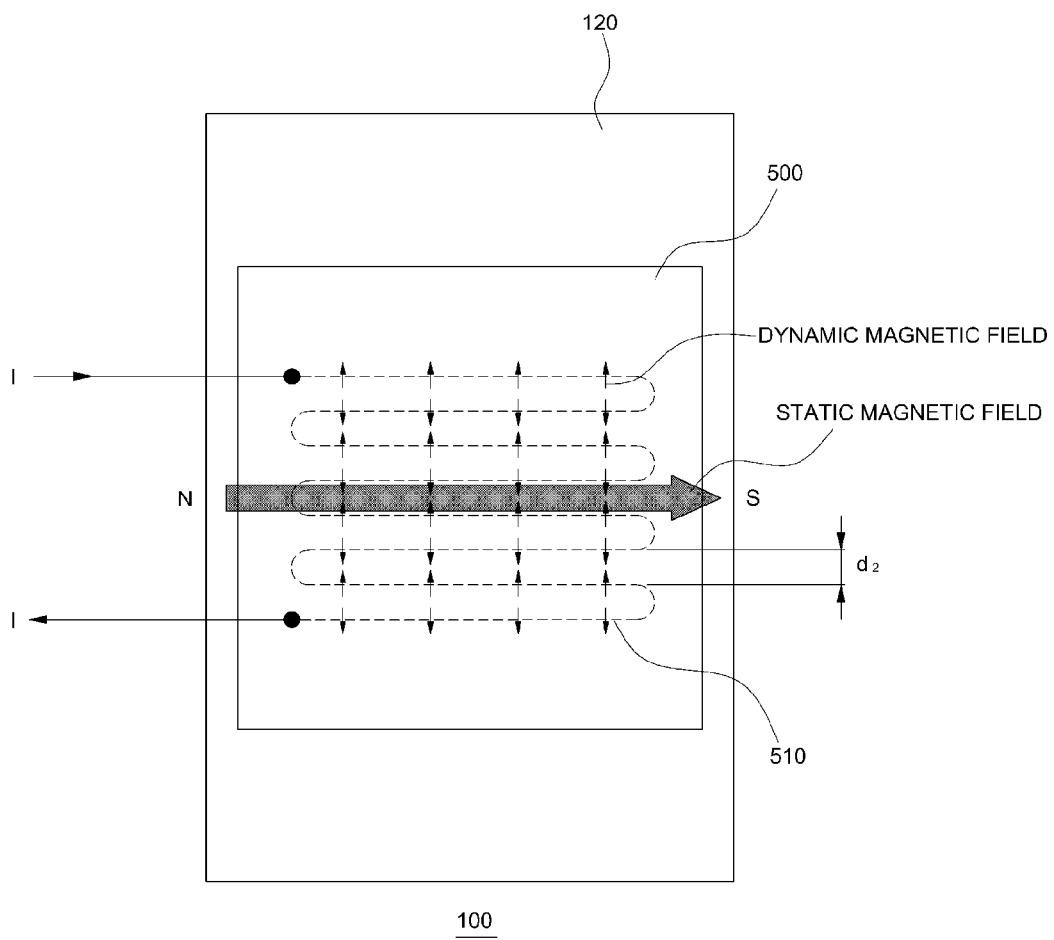
FIG. 3B is a side view of one of the plurality of magnetostrictive members in the magnetostrictive phased array transducer according to another embodiment of the present invention.

Meanwhile, another embodiment of the present invention will be described with reference to FIG. 3B. FIG. 3B is a side view of one of the plurality of magnetostrictive members in the MsPAT according to another embodiment of the present invention.

The MsPAT according to the embodiment of the present invention includes a plurality of magnetostrictive members 100 each having a bottom surface of a plate-shaped structure made of a ferromagnetic material, which is mounted to be adhered closely to the surface of a mounting place; an insulator 200 disposed on a side surface of each magnetostrictive member 100; a flexible printed circuit board 500 having a plurality of coil lines extended in the direction parallel with the bottom surface on each insulator 200, wherein adjacent coil lines are connected so that current flows in the opposite directions to each other, thereby generating a dynamic magnetic field with respect to each magnetostrictive member 100; and magnets 400a and 400b mounted to generate a static magnetic field perpendicular to the dynamic magnetic field. If the current is supplied to the flexible printed circuit board 500, the magnetostrictive members 100 generate a plurality of shear horizontal bulkwaves while being deformed by the magnetostriction effect.

In the embodiment of the present invention, it can be readily understood by those skilled in the art that descriptions of the magnetostrictive members 100, the magnets 400a and 400b and the yoke 600 are identical to those described above.

The flexible printed circuit board 500 is a flexible printed circuit board (FPCB) that a three-dimensional circuit board having flexibility. The flexible printed circuit board 500 generally refers to a circuit board formed by attaching a copper foil on an insulation film (polyimide) with a very thin thickness. The kind of the flexible printed circuit board 500 available in the present invention is not limited, and may be a single-face FPCB, double-face FPCB, multi FPCB, rigid PCB, etc.

As shown in FIG. 3B, the flexible printed circuit board 500 has a plurality of coil lines 510 extended in the direction parallel with the bottom surface of the magnetostrictive member 100, and adjacent coil lines 510 are connected so that current flows in the opposite directions to each other, thereby generating a dynamic magnetic field with respect to the magnetostrictive member 100. Since the coil lines 510 provided to the flexible printed circuit board 500 are printed on the flexible printed circuit board 500, the separate insulator 200 is not required as shown in FIG. 2, and the coil lines 510 may be disposed in the same manner as the coil lines of the meander coil 300. In the flexible printed circuit board 500, the distance $d_2$ between the adjacent coil lines 510 is preferably adjusted greater than or identical to a half of the wavelength of the generated shear horizontal bulkwave.

As described above, in the present invention, the static magnetic field generated by the magnets 400a and 400b and the dynamic magnetic field generated when the current is supplied to an electric wire connected to the flexible printed circuit board are perpendicular to each other, which causes deformation of the magnetostrictive member 100. Therefore, a plurality of shear horizontal bulkwaves are generated at the mounting place by the magnetostriction effect.

Figure 6:
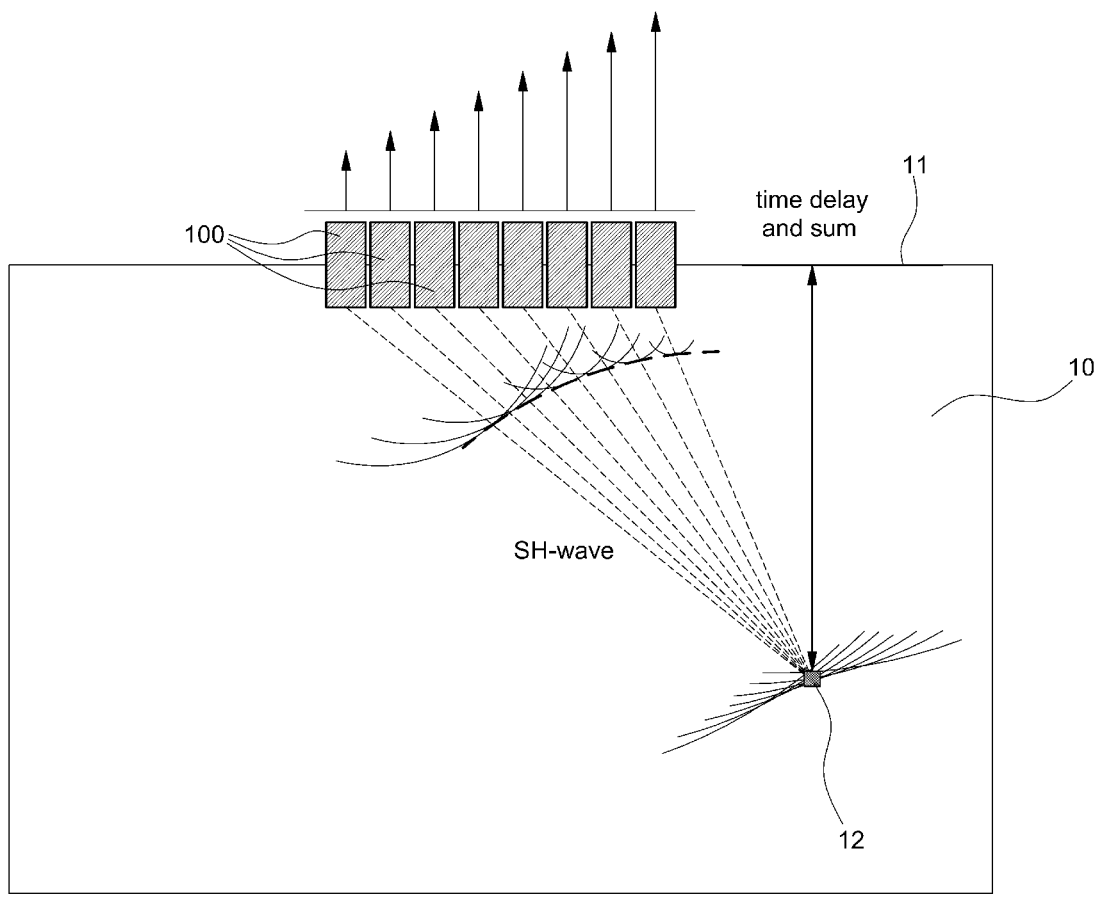
FIG. 6 is a schematic view illustrating a state in which the structure of a measurement sample is analyzed using the magnetostrictive phased array transducer.

Moreover, the analysis of a measurement sample by applying the present invention will be described with reference to FIG. 6. FIG. 6 is a schematic view illustrating a state in which the structure of a measurement sample is analyzed using the MsPAT.

As shown in FIG. 6, the MsPAT for transducing shear horizontal bulkwaves according to the present invention is disposed on a structure 10. The state of a surface 11 of the structure 10 may be flat or bent. The state of the surface 11 of the structure 10 is not particularly limited. However, the magnetostrictive member 100 is disposed to be adhered to the surface of the mounting place.

In the present invention, a plurality of magnetostrictive members generates a plurality of shear horizontal bulkwaves having a wide beam width with respect to the mounting place through the magnetostriction effect, and the user may process an image for the measurement sample using a plurality of shear horizontal bulkwaves when necessary. In the structure 10 shown in FIG. 6, it is assumed that the section having a defect portion 12 is divided into 100 rectangles having the same size, and a plurality of shear horizontal bulkwaves are focused with respect to the respective rectangles. When an image map is drawn by scanning signals for the respective rectangles, there exists a point at which a signal different from 99 signals can be obtained, and the user can identified that the point is the defect portion 12 through the present invention. In this case, since a plurality of shear horizontal bulkwaves are generated, the operation of each transducer is necessarily controlled to focus beans on a specific point through time-delay-and-sum processing. As shown in FIG. 6, a plurality of shear horizontal bulkwaves having the substantially same time interval difference (the length of an arrow) can be generated from each transducer by controlling current flowing in the meander coil on each magnetostrictive member. The advancing direction of the bulkwaves can be controlled by extending points that cause reinforcing interference, and the bulkwaves can be focused on a specific point.

As described above, in the MsPAT for transducing shear horizontal bulkwaves according to the present invention, a plurality of magnetostrictive members are used as a waveguide by being disposed to come in line contact with a measurement sample, so that it is possible to transduce a plurality of shear horizontal bulkwaves that form multiple channels while having a wide beam width in the direction of the measurement sample from a mounting place. Since the MsPAT can be mounted in a very small area without space limitation, the utilization of the MsPAT is high.

Further, beams can be focused on a specific point through time-delay-and-sum processing in each channel, and an image processed in a specific region of the measurement sample disposed in various points can be obtained using the focused beam signals and the scanning result for the focus of the beams. Particularly, the detection of a defect in the measurement sample can be effectively performed.

Further, the shear horizontal bulkwave having a frequency desired by a user can be transduced by adjusting the distance between adjacent coil lines.

Further, a flexible printed circuit board is used without additionally using an insulator and a meander coil, so that the MsPAT is advantageous in terms of lightweight, miniaturization, workability, convenience of manufacture, etc.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A magnetostrictive phased array transducer for transducing shear horizontal bulkwaves, the transducer comprising:
  a plurality of magnetostrictive members each having a bottom surface of a plate-shaped structure comprising a ferromagnetic material, wherein the bottom surface is mounted to be adhered within a predetermined distance to a surface of a mounting place;
  an insulator disposed on a side surface of each magnetostrictive member;
  a meander coil having a plurality of coil lines extended in a direction parallel with the bottom surface, on each insulator, wherein adjacent coil lines are connected so that current flows in opposite directions to each other, the meander coil is configured to generate a dynamic magnetic field with respect to each magnetostrictive member; and
  a magnet configured to generate a static magnetic field perpendicular to the dynamic magnetic field,
  wherein, when the current is supplied to the meander coil, the plurality of magnetostrictive members is configured to generate a plurality of shear horizontal bulkwaves while being deformed by a magnetostriction effect, and wherein the bottom surface of each of the magnetostrictive members is disposed to come in line contact with a measurement sample.

2. A magnetostrictive phased array transducer for transducing shear horizontal bulkwaves, the transducer comprising:

a plurality of magnetostrictive members each having a bottom surface of a plate-shaped structure comprising a ferromagnetic material, wherein the bottom surface is mounted to be adhered within a predetermined distance to a surface of a mounting place;

a flexible printed circuit board having a plurality of coil lines extended in a direction parallel with the bottom surface, on a side surface of each magnetostrictive member, wherein adjacent coil lines are connected so that current flows in opposite directions to each other, the plurality of coil lines is configured to generate a dynamic magnetic field with respect to each magnetostrictive member; and a magnet configured to generate a static magnetic field perpendicular to the dynamic magnetic field, wherein, when the current is supplied to an electric wire connected to the flexible printed circuit board, the plurality of magnetostrictive members is configured to generate a plurality of shear horizontal bulkwaves while being deformed by a magnetostriction effect, and wherein the bottom surface of each of the magnetostrictive members is disposed to come in line contact with a measurement sample.

3. The magnetostrictive phased array transducer of claim 1, wherein the time taken for each shear horizontal bulkwave to be focused with respect to the measurement sample is changed by adjusting a distance between the magnetostrictive members.

4. The magnetostrictive phased array transducer of claim 1, wherein a focusing direction of the shear horizontal bulkwaves with respect to the measurement sample is changed by controlling a difference in time at which each magnetostrictive member generates a shear horizontal bulkwave.

5. The magnetostrictive phased array transducer of claim 1, further comprising a couplant filled in an empty space between the bottom surface of each magnetostrictive member and the surface of the mounting place.

6. The magnetostrictive phased array transducer of claim 1, further comprising a rear member configured to perform a damping process on the magnetostrictive member.

7. The magnetostrictive phased array transducer of claim 1, wherein, for each magnetostrictive member an area of a surface opposite to the bottom surface is formed narrower than that of the bottom surface to induce and offset diffused reflection of ultrasonic waves.

8. The magnetostrictive phased array transducer of claim 1, wherein, for each magnetostrictive member a surface opposite to the bottom surface is formed in a saw-tooth shape to induce and offset diffused reflection of ultrasonic waves.

9. The magnetostrictive phased array transducer of claim 1, further comprising a yoke attached to the magnet to form a loop of the static magnetic field.

10. The magnetostrictive phased array transducer of claim 2, wherein the time taken for each shear horizontal bulkwave to be focused with respect to the measurement sample is changed by adjusting a distance between the magnetostrictive members.

11. The magnetostrictive phased array transducer of claim 2, wherein a focusing direction of the shear horizontal bulkwaves with respect to the measurement sample is changed by controlling a difference in time at which each magnetostrictive member generates a shear horizontal bulkwave.

12. The magnetostrictive phased array transducer of claim 2, further comprising a couplant filled in an empty space between the bottom surface of each magnetostrictive member and the surface of the mounting place.

13. The magnetostrictive phased array transducer of claim 2, further comprising a rear member configured to perform a damping process on the magnetostrictive member.

14. The magnetostrictive phased array transducer of claim 2, wherein, for each magnetostrictive member an area of a surface opposite to the bottom surface is formed narrower than that of the bottom surface to induce and offset diffused reflection of ultrasonic waves.

15. The magnetostrictive phased array transducer of claim 2, wherein, for each magnetostrictive member a surface opposite to the bottom surface is formed in a saw-tooth shape to induce and offset diffused reflection of ultrasonic waves.

16. The magnetostrictive phased array transducer of claim 2, further comprising a yoke attached to the magnet to form a loop of the static magnetic field.

* * * * *